United States Patent [19]
Bass

[11] Patent Number: 5,681,164
[45] Date of Patent: Oct. 28, 1997

[54] ORTHODONTIC APPLIANCE

[76] Inventor: Neville Meyer Bass, 4, Queen Anne Street, London W1M 9LE, England

[21] Appl. No.: 403,707
[22] PCT Filed: Jul. 21, 1994
[86] PCT No.: PCT/GB94/01580
§ 371 Date: May 30, 1995
§ 102(e) Date: May 30, 1995
[87] PCT Pub. No.: WO95/03005
PCT Pub. Date: Feb. 2, 1995

[30] Foreign Application Priority Data

Jul. 22, 1993 [GB] United Kingdom .............. 9315157

[51] Int. Cl.⁶ .................................................. A61C 3/00
[52] U.S. Cl. .................................... 433/6; 5/7; 5/17
[58] Field of Search ........................ 433/5, 6, 7, 18, 433/21, 17

[56] References Cited

U.S. PATENT DOCUMENTS

| | | |
|---|---|---|
| 4,416,625 | 11/1983 | Armstrong . |
| 4,468,196 | 8/1984 | Keller .................................. 433/7 |
| 4,571,178 | 2/1986 | Rosenburg .......................... 433/18 |
| 4,573,914 | 3/1986 | Nord ................................... 433/18 |
| 4,752,222 | 6/1988 | Bass .................................... 433/6 |
| 5,299,935 | 4/1994 | Lokar ................................. 433/18 |

FOREIGN PATENT DOCUMENTS

| | | |
|---|---|---|
| 2941569 | 4/1981 | Germany . |
| 2192339 | 1/1988 | United Kingdom . |

*Primary Examiner*—Cary E. O'Connor
*Attorney, Agent, or Firm*—Baker & Botts, L.L.P.

[57] ABSTRACT

An orthopaedic modular assembly comprises a housing component of rigid material providing a first passage, a second component in the form of a lingual pad support having a first arm adapted to form a sliding fit within the first housing passage and a second arm extending at an angle to the first arm and adapted to conform to the line of the one side of a patient's mouth and a latch associated with the housing component, whereby the first arm of the second component is held within the first passage of the housing component by the latch and is slidably adjustable relative to the housing component to any one of a plurality of predetermined latched positions. The sliding lingual pad component is locked simply and securely in the housing component and is able to be moved forward in precise increments relative to the housing as treatment progresses.

15 Claims, 6 Drawing Sheets

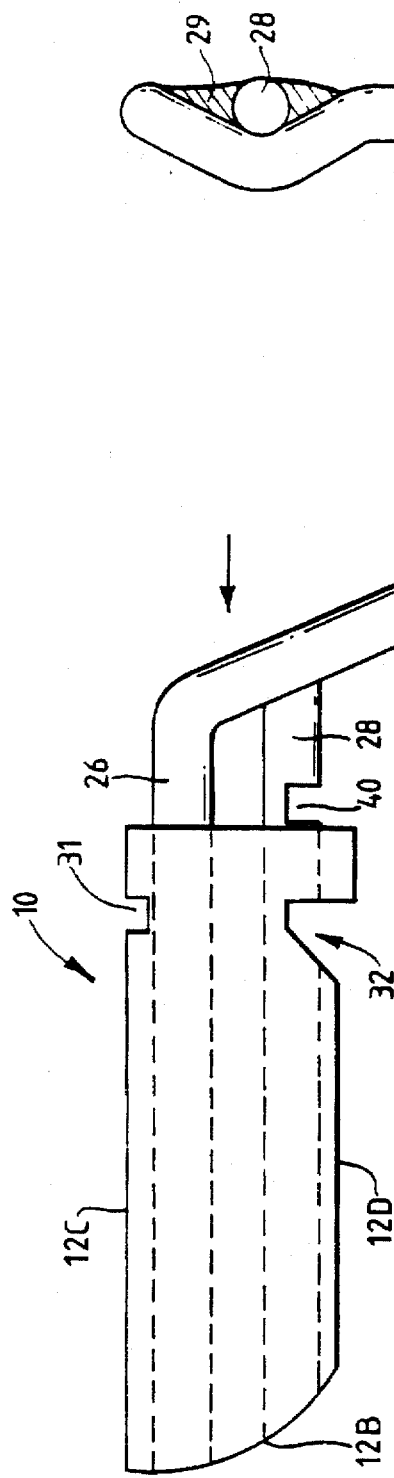
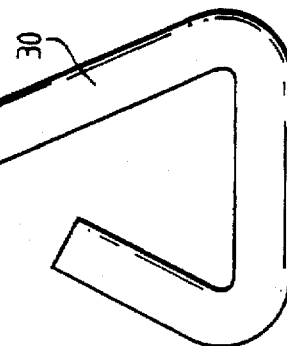
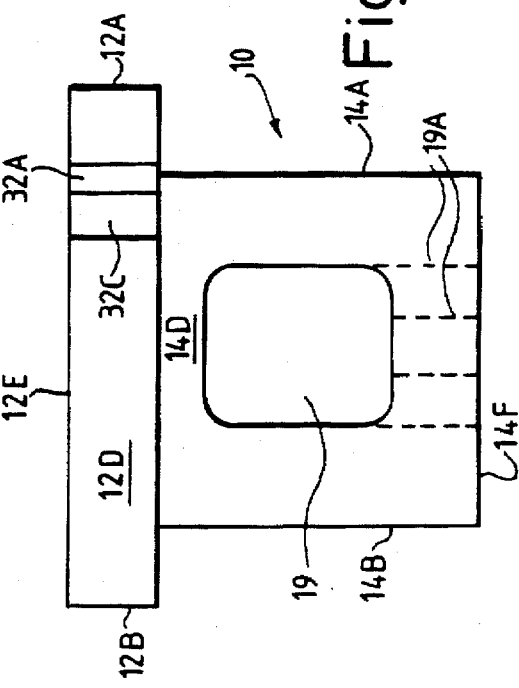
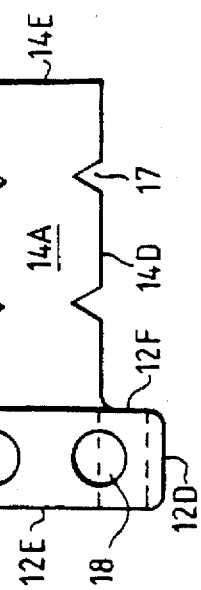
Fig.11.
Fig.10
Fig.12.
Fig.13.

ORTHODONTIC APPLIANCE

This invention relates to an orthopaedic modular assembly for application to one side of a patient's mouth and to a dento-facial orthodontic appliance comprising two such assemblies.

My British Patent No. 2 192 339 describes an orthopaedic modular assembly comprising a housing component of rigid material providing a first vertically spaced pair of parallel passages and a second horizontally spaced pair of parallel passages extending substantially at right angles to said first pair, a second component in the form of a lingual pad support having a pair of parallel arms adapted to form a snug sliding fit within said first pair of housing passages and a further arm extending substantially at right angles to said pair of arms and adapted to conform to the line of one side of a patient's mouth, and a third component having a pair of parallel members adapted to fit within said second pair of housing passages and a portion extending upwardly at an angle to said members for supporting a member designed to act on the cheek at said one side of the patient's mouth.

One problem associated with the modular assembly described above is that in order to secure the arms of the lingual pad support in the housing it is necessary to squeeze the arm where it is received in the passage of the housing to provide a friction fit. This is not only a difficult procedure but also does not provide a very secure attachment to the housing.

It is one object of the present invention to provide an orthopaedic modular assembly in which the above mentioned disadvantage associated with my previous assembly is obviated or at least mitigated. In particular it is one object of the present invention to provide such a modular assembly comprising a housing component which forms a fixed support for a lingual pad support wherein the lingual pad support is held securely in the housing and may be inserted or removed therefrom in a simple and convenient manner.

It is another object of the present invention to provide an improved orthodontic appliance comprising two such modular assemblies.

It is a further object of the present invention to provide an orthopaedic modular assembly which is simple and cheap to manufacture.

The present invention accordingly provides an orthopaedic modular assembly comprising a housing component of rigid material providing a first passage, a second component in the form of a lingual pad support having a first arm adapted to form a snug sliding fit within the first housing passage and a second arm extending at an angle to said first arm and adapted to conform to the line of one side of a patient's mouth, and latch means associated with the housing component wherein the second component is held in the housing component by the latch means and is slidably adjustable relative to the housing to any one of a plurality of predetermined latched positions.

The latch means preferably comprises a resilient member, such as a spring, which is attached to the housing and arranged to engage one of a plurality of notches formed in the first arm of the lingual pad support.

The housing may be provided with a second passage vertically spaced from and parallel to the first passage and the lingual pad support may be provided with a second arm extending parallel to the first arm, the pair of parallel arms being adapted to form a snug sliding fit within the first and second housing passages.

Suitably, the housing is provided with a horizontally spaced pair of parallel passages or channels extending substantially at right angles to the first passage and a third component is provided having a pair of parallel arms adapted to fit within the horizontally spaced pair of housing passages or channels and a portion extending upwardly at an angle to the arms for supporting a member designed to act on the cheek at one side of the patient's mouth.

The housing is preferably formed of synthetic plastics material and injection moulded in one piece. Alternatively, the housing maybe formed of metal such as stainless steel. The housing may be provided with integral mounting sockets adapted to receive the ends of a demountable headgear to allow applications of force from outside the mouth. Alternatively, the mounting socket may be provided on a separate support as disclosed in my above mentioned British Patent.

With the present invention it is possible to lock the sliding lingual pad component simply and securely in the housing and also to move the component forwardly in precise increments relative to the housing as treatment progresses.

An embodiment of the present invention will now be described, by way of example, with reference to the accompanying drawings, in which:

FIG. 3 is a plan view of the housing component of the first assembly;

FIG. 10 is a side view of a third left-hand modular assembly in accordance with the invention;

FIG. 11 is a front end view of the lingual pad support of the third assembly looking in the direction of the arrow in FIG. 10;

FIG. 12 is a front end view of the housing component of the third assembly; and

FIG. 13 is a bottom plan view of a left-hand housing component of a fourth left-hand modular assembly.

The left-hand assemblies shown in the Figures are designed for use in combination with respective right-hand assemblies which are a mirror-image of themselves, in the construction of an orthodontic appliance.

Figure 1:
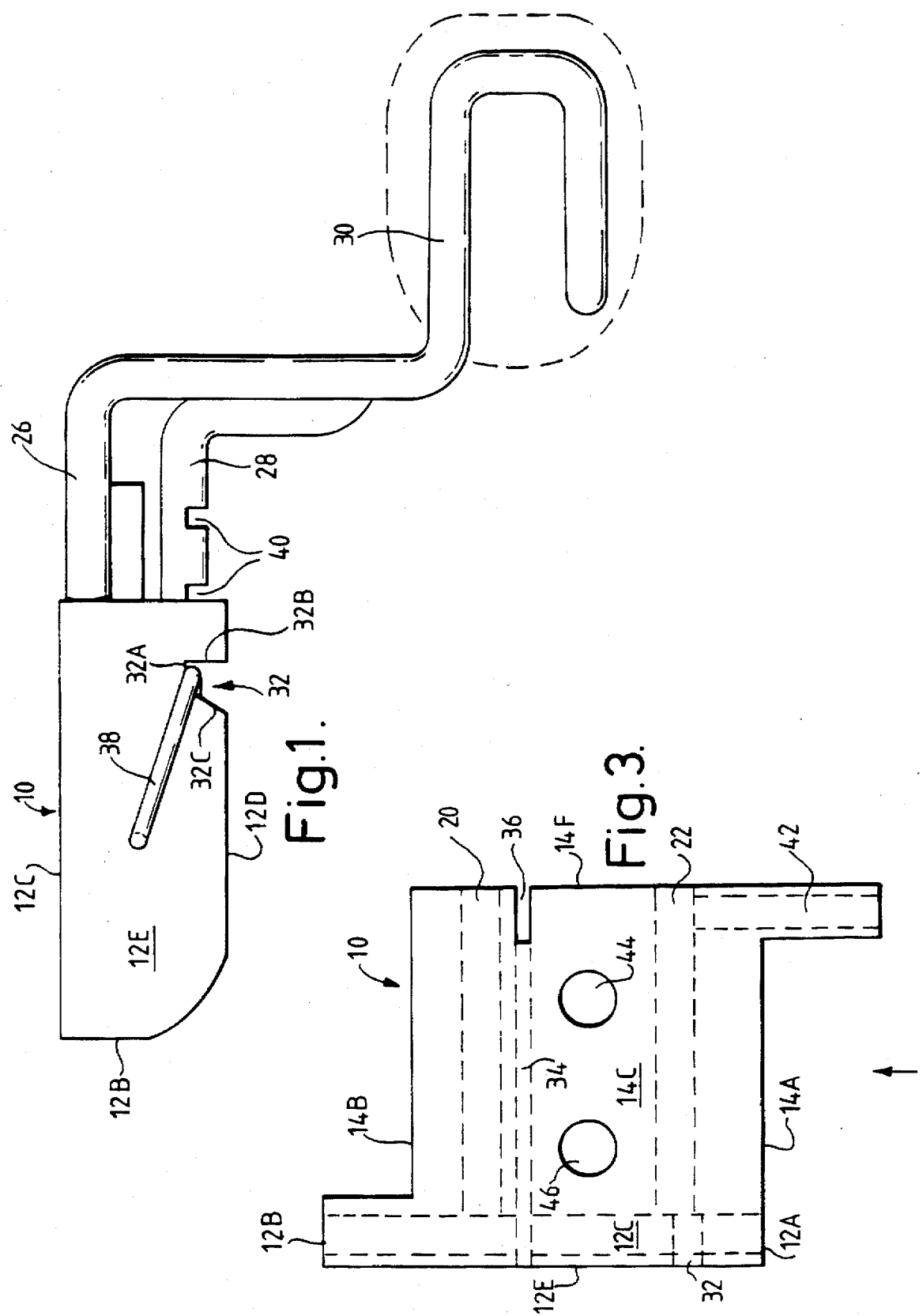
FIG. 1 is a side view of a first left-hand modular assembly in accordance with the invention.
Figure 2:
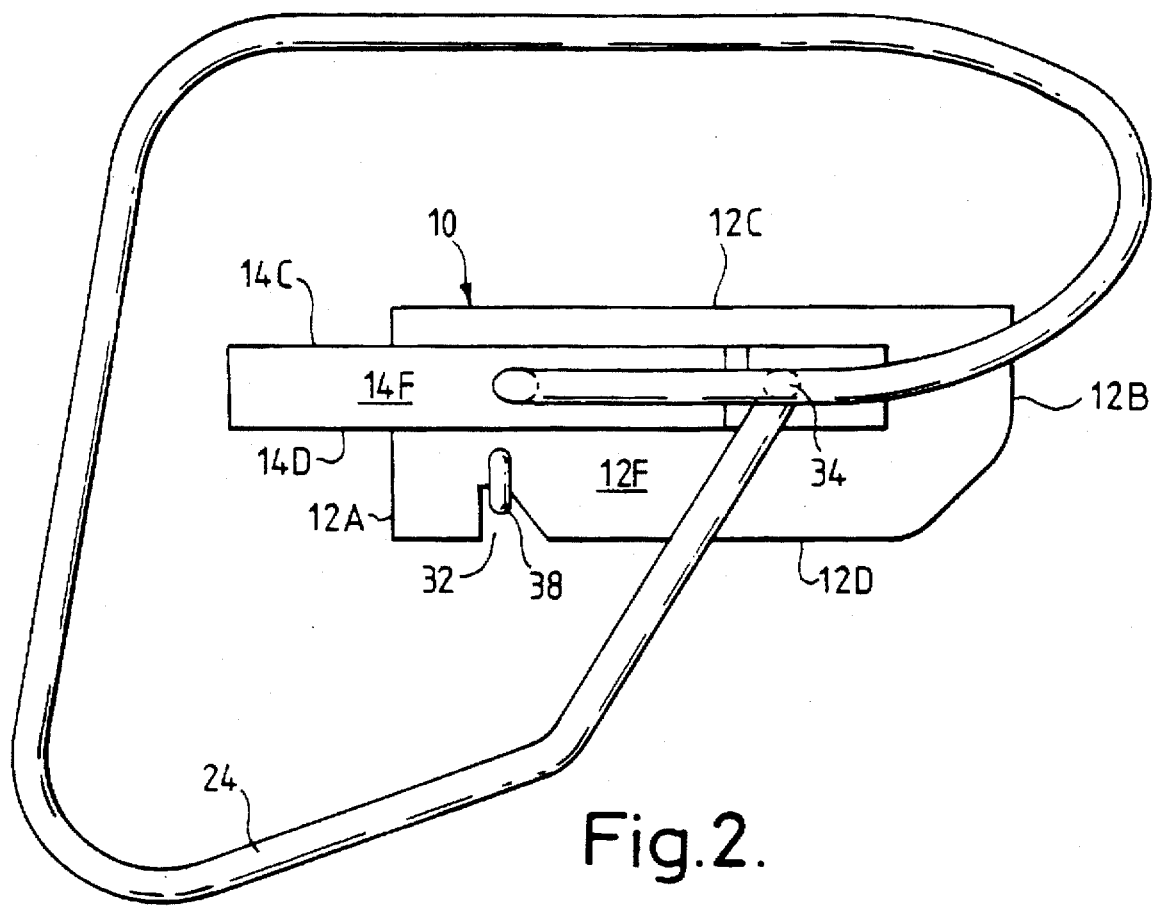
FIG. 2 is a view of the opposite side of the assembly of FIG. 1.
Figure 4:
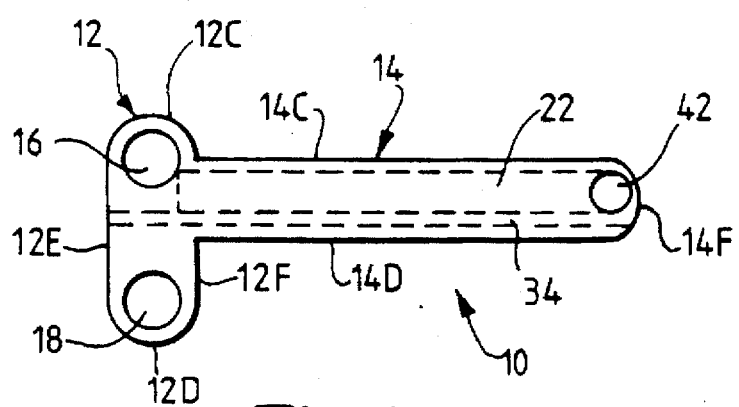
FIG. 4 is an end view of the first assembly looking in the direction of the arrow in FIG. 3.

Referring first to the assembly shown in FIGS. 1 to 4, this assembly includes a housing component 10 formed of stainless steel having a vertical portion 12 and an integral horizontal portion 14. The vertical portion 12 generally has front 12A, rear 12B, upper 12C, lower 12D, and inner and outer side, 12E and 12F, surfaces. The horizontal portion 14 generally has front 14A, rear 14B, upper 14C, lower 14D, and outer side 14F surfaces. The vertical portion 12 of the housing 10 comprises parallel passages 16, 18 (FIG. 4) and the horizontal portion 14 of the housing 10 comprises parallel passages 20, 22 (FIG. 3) which extend at right angles to the passages 16, 18. The housing component may comprise tubes as illustrated in my above mentioned British Patent instead of the present block of material with passages. The passages 20, 22 slidably receive parallel prongs (not shown) on member 24 (side screen) of stainless steel wire, (synthetic plastics may be added to the side screen (not shown)) to move the cheek muscles laterally and thereby permit expansion of dental arches and artificially provide the correct matrix for development of dental occlusion. The passages 16, 18 slidably receive the parallel arms 26, 28 of a component 30, made of stainless steel wire, to develop an avoidance reflex of the lower jaw and accelerate its growth. The component 30 may be used with or without a lingual pad (shown with dashed lines in FIG. 1). A downwardly opening slot 32 is provided in the lower surface 12D of the vertical portion 12 of the housing 10 which extends transversely through the passage 18. In FIGS. 1 and 2, the slot is seen to have a base 32A, one side 32B perpendicular to the base and another side 32C at an obtuse angle to the base 32A. A bore 34 extends through the housing 10 parallel to the passages 20, 22 and is open at both ends to respective inner 12E and outer 14F side surfaces of the housing. At the outer side surface 14F the bore 34 opens out into the base of a cut-out 36 in the outer edge of the horizontal portion 14. A substantially U-shaped metal spring 38 extends through the bore 34, along the inner side surface 12E of the vertical portion 12 of the housing 10 and across the slot 32, one end of the spring being attached to a wall of the cut-out 36 and the other end being attached adjacent the slot 32 at the outer side surface 12F of the vertical portion 12 (FIG. 2). The spring 38 bears against the slanted side 32C of the slot 32 and extends transversely through the passage 18. Lower arm 28 of the lingual pad support 30 is formed with a series of notches 40 spaced longitudinally at intervals of 2 mm. When the arm is slid into engagement with the passage 18 and one of the notches 40 is aligned with the slot 32, the spring 38 engages the notch 40 to hold the arm 28 securely in a fixed position. The arm 28 may be slid forwardly or rearwardly to allow the spring 38 to engage any selected one of the notches 40.

The housing 10 also includes a passage 42 for receiving the inner end of a demountable headgear attachment (not shown) designed to allow applications of force from outside the mouth to retard and control growth of the maxilla and to control eruption of molar teeth.

FIGS. 5 to 13 illustrate alternative assemblies of the present invention. For simplicity, in FIGS. 5 to 13 the same reference numerals to those used in FIGS. 1 to 4 have been used to illustrate the same or similar parts.

Figure 5:
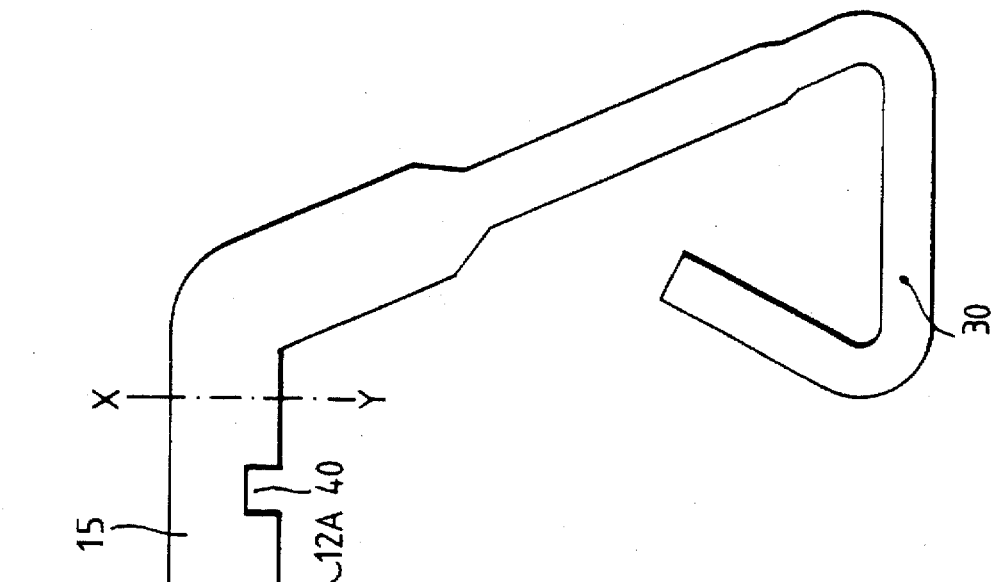
FIG. 5 is a side view of a second left-hand modular assembly in accordance with the invention.
Figure 6:
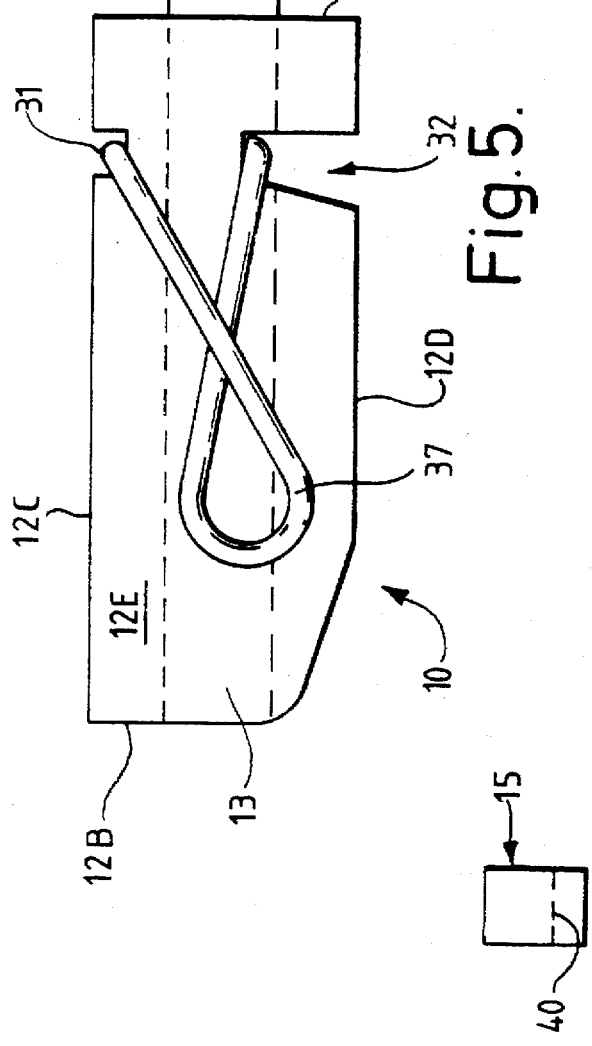
FIG. 6 is a cross sectional view of the lingual pad support in FIG. 5 taken along the line X-Y.
Figure 7:
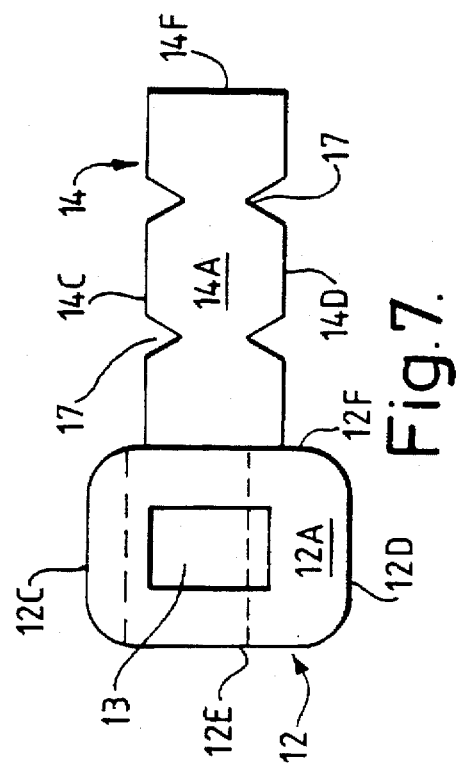
FIG. 7 is a front end view of the housing component of the second assembly.
Figure 8:
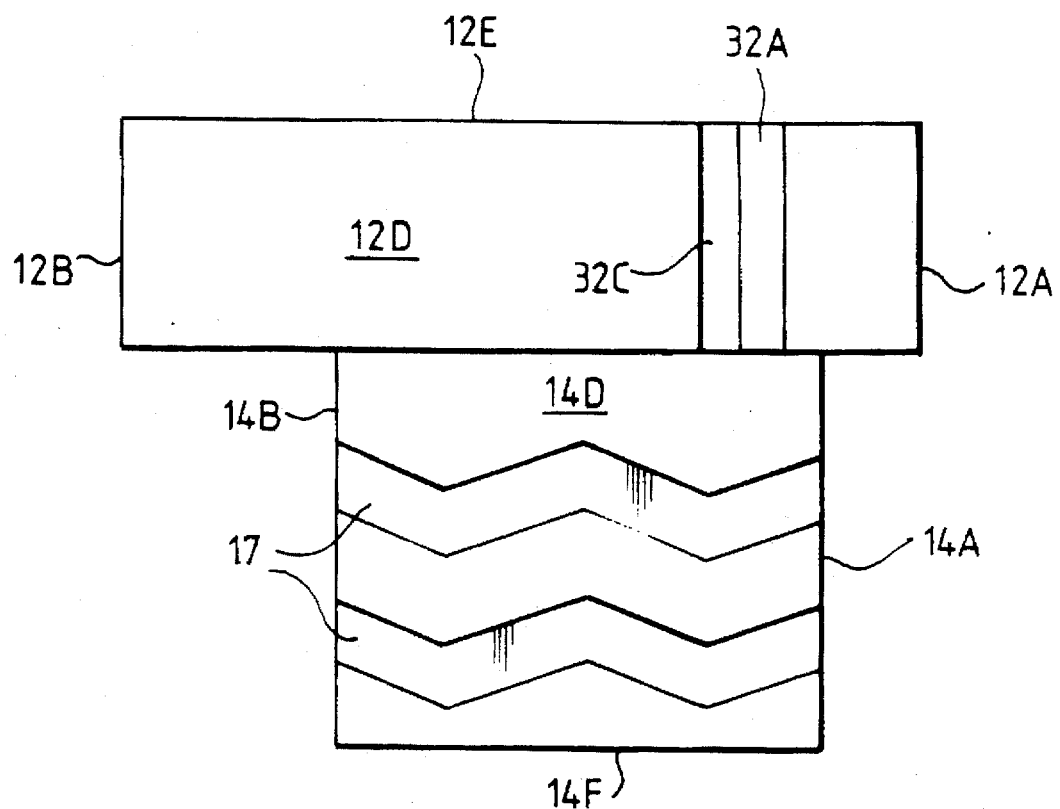
FIG. 8 is a bottom plan view of the housing component of the second assembly.

The assembly shown in FIGS. 5 to 9 includes a housing component 10 formed of synthetic plastics material, such as acrylic, in one piece by injection moulding. The vertical portion 12 of the housing is provided with a single passage 13, which is rectangular in cross-section as shown in FIG. 7. A lingual pad support 30 has a single arm 15 which is slidably mounted in the passage 13 of the housing 10. The arm 15 of the lingual pad support is rectangular in cross-section and dimensioned to be a close fit within the correspondingly shaped passage 13 so that any rotation of the arm 15 relative to the housing 10 is avoided. A downwardly opening slot 32 is provided in the lower surface 12D of the vertical portion 12 of the housing 10 which extends transversely through the passage 13. Directly above the slot 32 a cut-out 31 is provided in the upper-surface 12C of the vertical portion 12 of the housing. A looped metal spring 37 lies adjacent the inner side surface 12E of the vertical portion 12 and has first and second free end portions which are bent to hook over slot 32 and cut-out 31, respectively. When mounted on the housing 10 as shown in FIG. 5, the spring 37 is biased so that its ends firmly engage the slot 32 and cut-out 31 without additional fastening means. The first end portion of the spring 37 extends transversely through the passage 32 in the housing 10 and engages a notch 40 in the arm 15 of the lingual pad support when the notch 40 is in alignment with the slot 32, thereby retaining the arm 15 and hence the lingual pad support securely in a fixed position relative to the housing 10.

Figure 9:
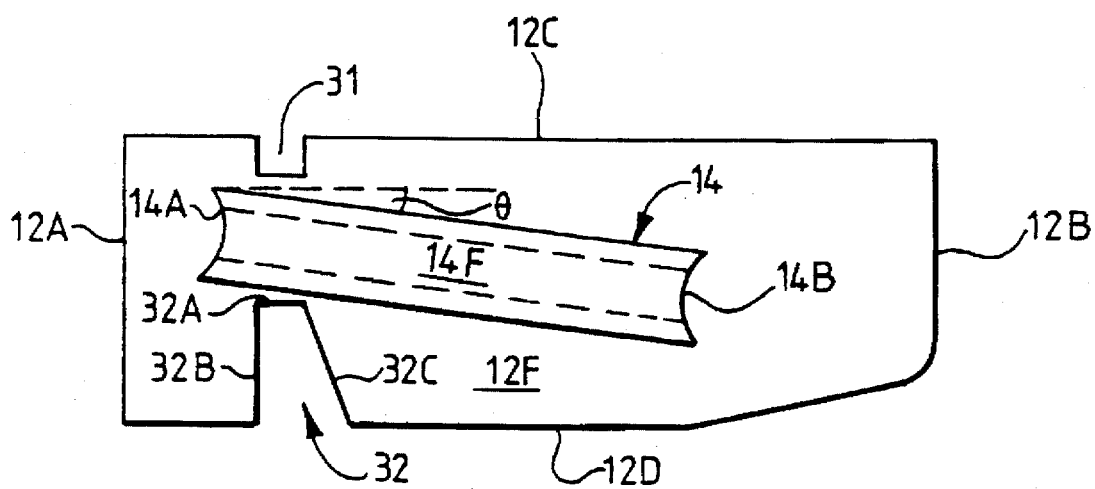
FIG. 9 is a view of the opposite side of the housing component of the second assembly.

In FIG. 9 the horizontal portion 14 is seen to slope downwardly from the front end to the rear end of the housing 10 at an angle θ of 7° relative to the upper surface 12C of the vertical portion 12. The front 14A and rear 14B edges of the horizontal portion 14 are in the form of concave channels to partly receive respective parallel prongs on a side screen member (not shown) for acting on the cheek muscles. The prongs are secured in position by plastics former in which the assembly is eventually embedded.

The upper 14C and lower 14D surfaces of the horizontal portion 14 of the housing 10 are provided with zig-zag grooves 17 which serve to retain the housing 10 in the former.

The synthetic plastics housing component 10 illustrated in FIGS. 5 to 9 may, as an alternative to being provided with the single passage, be provided with two vertically spaced parallel passages 16 and 18, as in the assembly illustrated in FIGS. 10 to 12. The passages 16 and 18 are circular in cross-section to receive respective first and second correspondingly shaped parallel arms 26 and 28 of a lingual pad support 30. The second arm 28 of the lingual pad support is formed with a series of longitudinally spaced notches 40 and is connected to the downwardly extending arm 30 of the lingual pad support by silver solder 29 (FIG. 11).

The housing component shown in FIG. 10 may alternatively be formed of stainless steel except that the zig-zag grooves in the horizontal portion are replaced with an aperture 19 (FIG. 13) to retain the housing 10 in the acrylic former. Instead of the aperture 19 the whole of the central portion may be removed as is shown by the dashed lines 19A.

A constructed orthodontic appliance for use in the mouth to correct dental malocclusion resulting from a lack of forward growth of the mandible in an individual patient is illustrated in my above mentioned British Patent and the present appliances would be constructed in the same manner. Briefly described, a left-hand modular assembly of the kind illustrated and a right-hand modular assembly constructed as a mirror-image of the left-hand assembly are arranged so that, in use, the passages 20, 22 or channels 14A, 14B extend transversely of and beneath the upper back teeth of the patient and the members 24, arranged in the outer ends of the passages or channels, form a pair of left- and right-hand side screens preformed from stainless steel or synthetic plastics material to act on the patient's cheeks. The components 30 of the assemblies, are deformed to conform to the sides of the patient's mouth and may support a pair of left- and right-hand lingual pads, in positions to stimulate forward posturing of the mandible in the individual patient. The free ends of the arms 30 are bent to form hooks which enter blind bores in the pads or may act as the pads themselves. The slidable mounting of the arms 26 and 28 or 15 in the passages 16 and 18 or 13 enables the lingual pads to maintain stimulation by forward adjustment as jaw growth proceeds. The modular assemblies are embedded in a plastics former which follows the lines of the teeth. Apertures 44, 46 or 19 which pass through, and grooves 17 which are formed in the upper and lower surfaces 14C, 14D of the horizontal portion 14 of the housing 10, are filled with plastic resin and serve to retain the housing in the former.

Each of the side screens may be formed with a bore to receive one end of an elongate support formed from wire or synthetic plastics material, for a pair of pre-formed labial pads formed from synthetic plastics material and designed to act on the lip muscles of the patient.

Figure 14:
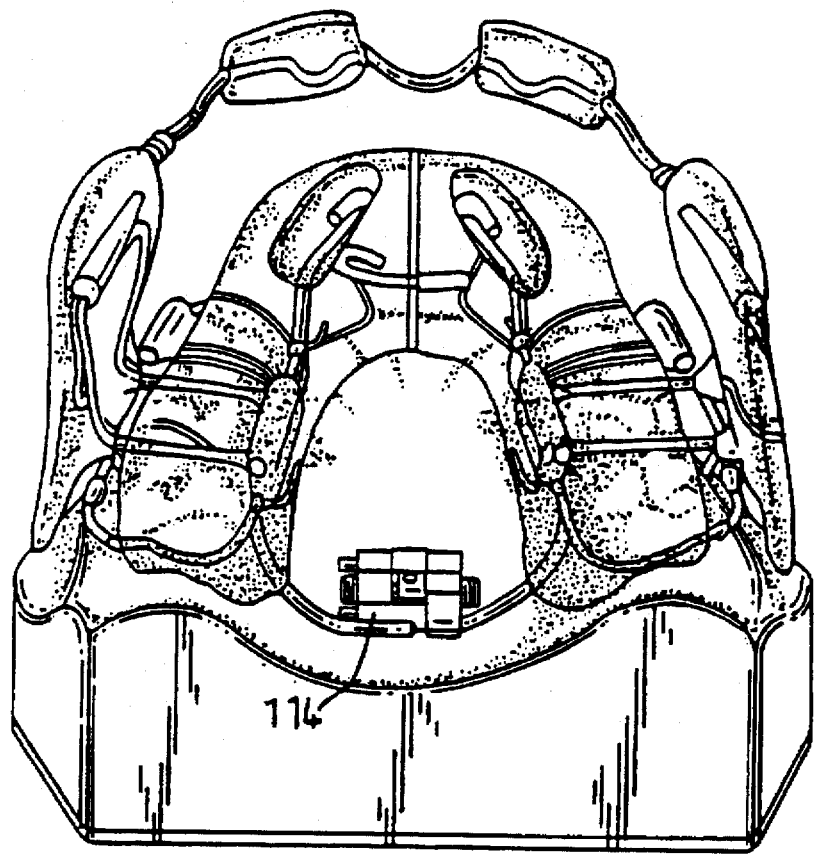
FIG. 14 is a rear perspective view of a known orthodontic appliance disclosed in British Patent No. 2,192,339 for use in the upper part of a patient's mouth and incorporating two modular assemblies.
Figure 15:
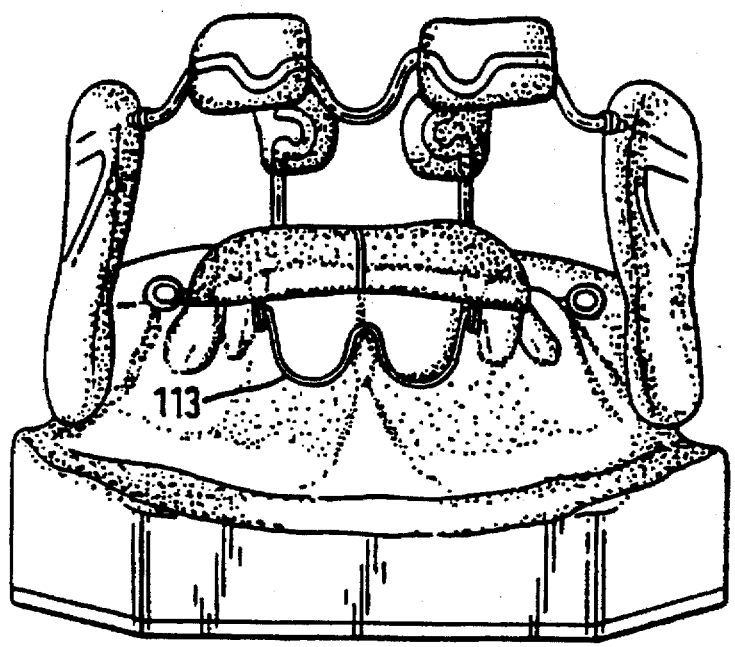
FIG. 15 is a front perspective view of the appliance depicted in FIG. 14.

As with my previous appliance, as depicted in FIG. 15, a torque spring 113 may be provided at the front and, as depicted in FIG. 14 an expansion screw 114 or spring attached to the central portion of the appliance.

It should be understood that various modifications, changes and variations may be made in the arrangement and details of construction of the elements disclosed herein without departing from the scope of this invention. As an alternative to the arm or arms of the lingual pad support being mounted in passages formed in the housing by latch means, they may be mounted on screws attached to the upper part of the appliance to permit forward adjustment. As a further alternative, the lingual pads may be attached to the main body of the appliance with fixed wires incorporating loops to permit forward adjustment.

I claim:

1. An orthopaedic modular assembly comprising a housing component of rigid material providing a first passage, a second component in the form of a lingual pad support having a first arm adapted to form a snug sliding fit within the first housing passage and a second arm extending at an angle to said first arm and adapted to conform to the line of one side of a patient's mouth and latch means associated with the housing component, whereby the first arm of the second component is held within the first passage of the housing component by the latch means and is slidably adjustable relative to the housing component to any one of a plurality of predetermined latched positions.

2. An assembly according to claim 1, wherein the latch means comprises a resilient member arranged to engage one of a plurality of notches formed in the first arm of the lingual pad support.

3. An assembly according to claim 2, wherein the resilient member is a spring.

4. An assembly according to claim 1, wherein the first passage is substantially rectangular in cross-section.

5. An assembly according to claim 1, wherein the housing component is formed with a second passage vertically spaced from and parallel to the first passage and the lingual pad support has a third arm extending parallel to the first arm, said pair of parallel arm being adapted to form a snug sliding fit within the vertically spaced pair of housing passages.

6. An assembly according to claim 1, wherein the housing component is formed with a horizontally spaced pair of passages or channels extending substantially at right angles to the first passage and a third component having a pair of parallel arms adapted to fit within the horizontally spaced pair of housing passages or channels and a portion extending upwardly from said arms at an angle to said arms for supporting a member designed to act on the cheek at one side of the patient's mouth.

7. An assembly according to claim 1, wherein the lingual pad support is adjustable forwardly relative to the housing component as jaw growth proceeds.

8. An assembly according to claim 1, wherein the material of which the housing component is made is selected from the group consisting of synthetic plastics and stainless steel.

9. An assembly according to claim 8, wherein the housing is moulded in one piece.

10. An assembly according to claim 8, wherein the housing is cast in one piece.

11. An assembly according to claim 1, wherein the housing is formed with integral mounting sockets adapted to receive the ends of a demountable headgear to allow applications of force from outside the mouth.

12. An orthodontic appliance comprising two modular assemblies as claimed in claim 1, adjusted to the shape of the left-and right-hand sides respectively of a patient's mouth, a layer of synthetic plastics material formed to the shape of the patient's mouth and serving to fix said assemblies in position relative to one another and in correct relationship to the patient's mouth.

13. An appliance according to claim 12, further comprising a plurality of components designed to act on selected parts of the patient's face and adjustably supported by the assemblies and the plastics layer.

14. An appliance according to claim 12, provided at its forward end with a torque spring for controlling movement of the roots of the upper front teeth of the patient and assisting in retaining the appliance in place on the patient's teeth.

15. An appliance according to claim 12, including an expansion screw operable on said modular assemblies to adjust the width of the appliance.

* * * * *